US009140660B2

(12) United States Patent
Yang et al.

(10) Patent No.: US 9,140,660 B2
(45) Date of Patent: Sep. 22, 2015

(54) HIGH PRESSURE REFERENCE ELECTRODE AND A METHOD TO ELIMINATE THE FORMATION OF GAS BUBBLES IN VERTICAL OR SLOPED LIQUID-FILLED TUBES

(71) Applicants: Lietai Yang, San Antonio, TX (US); Xiaodong Sun Yang, San Antonio, TX (US)

(72) Inventors: Lietai Yang, San Antonio, TX (US); Xiaodong Sun Yang, San Antonio, TX (US)

( * ) Notice: Subject to any disclaimer, the term of this patent is extended or adjusted under 35 U.S.C. 154(b) by 0 days.

(21) Appl. No.: 13/731,911

(22) Filed: Dec. 31, 2012

(65) Prior Publication Data

US 2013/0213808 A1 Aug. 22, 2013

Related U.S. Application Data

(62) Division of application No. 12/290,388, filed on Oct. 30, 2008, now Pat. No. 8,377,276.

(51) Int. Cl.
*G01N 27/403* (2006.01)
*B01D 19/00* (2006.01)
*G01N 27/30* (2006.01)

(52) U.S. Cl.
CPC .................................. *G01N 27/301* (2013.01)

(58) Field of Classification Search
USPC ............... 204/435, 433, 416; 261/105, 109, 261/114.2, 126; 324/437, 438, 446–449, 324/450
See application file for complete search history.

(56) References Cited

U.S. PATENT DOCUMENTS

| 4,116,798 | A | * | 9/1978 | Magar et al. ................ 204/408 |
| 4,273,637 | A | | 6/1981 | MacDonald et al. |
| 4,288,683 | A | * | 9/1981 | Will ............................ 392/331 |
| 5,795,061 | A | * | 8/1998 | Perlman ...................... 366/130 |

OTHER PUBLICATIONS

D. D. MacDonald, "Reference Electrodes for High Temperature Aqueous Systems—A Review and Assessment," Corrosion, vol. 34, p. 75-84, 1978.
A.K. Agrawal and R.W. Staele, "A Silver-Silver Chloride Reference Electrode for the High Temperature and High Pressure Electrochemistry," Corrosion, vol. 33, p. 418-419, 1977.
S. H. Oh, C.B. Bahn, and I. S. Hwang, "Evaluation of Thermal Liquid Junction Potential of Water-Filled External Ag/AgCl Reference Electrodes," Journal of the Electrochemical Society, vol. 150, p. E321-E328, 2003.
C.M. Menedez, "Reference Electrodes for High Pressure and High Temperature Electrochemical Testing," Corrosion/2001, paper, 01305, (Houston, TX: NACE International, 2001).

* cited by examiner

*Primary Examiner* — Alex Noguerola

(57) ABSTRACT

A method for preventing the formation of gas bubbles inside a high pressure reference electrode in the electrolyte-filled section, and thus eliminating the gas bobble effect on the electrical continuity, was disclosed. One or more thin solid rods or tubes are inserted into the internal electrolyte-housing tube and the thin rods or tubes alter the surface tension of the gas bubbles so that the bubbles are unstable in the middle of the liquid electrolyte. Compared with the fiber wicks or porous powder used by previous researchers to ensure the electrical continuity, the thin tubes or rods are easy to handle and easy to clean. This method may also be used in other systems that contain a liquid-filled vertical or sloped tube (e.g., a pH electrode) to prevent the formation of gas bubbles in the liquid-filled section of the tube.

15 Claims, 3 Drawing Sheets

HIGH PRESSURE REFERENCE ELECTRODE AND A METHOD TO ELIMINATE THE FORMATION OF GAS BUBBLES IN VERTICAL OR SLOPED LIQUID-FILLED TUBES

CROSS-REFERENCE TO RELATED APPLICATIONS

This is a division of application Ser. No. 12/290,388, filed on Oct. 30, 2008, now allowed.

TECHNICAL FIELD OF THE INVENTION

This invention relates to pressure-balanced reference electrodes and pH electrodes for high-pressure applications.

BACKGROUND OF THE INVENTION

High-pressure and high-temperature reference electrodes are widely used for corrosion control and electrochemical studies [see D. D. Macdonald, "Reference Electrodes for High Temperature Aqueous Systems—A Review and Assessment," *Corrosion*, Vol. 34, page 75-84, 1978, and C. M. Menendez, "Reference Electrodes For High Pressure And High Temperature Electrochemical Testing," *CORROSION/2001*, paper, 01305, (Houston, Tex.: NACE International, 2001)]. This invention is related to a method for eliminating the formation of gas bubbles inside a reference or a pH electrode tube filled with a liquid. Such gas bubbles formed inside the tube in the liquid section often affect the electrical continuity between the top and bottom ends of an electrode.

REFERENCE NUMBERS OF DRAWINGS

Figure 1:
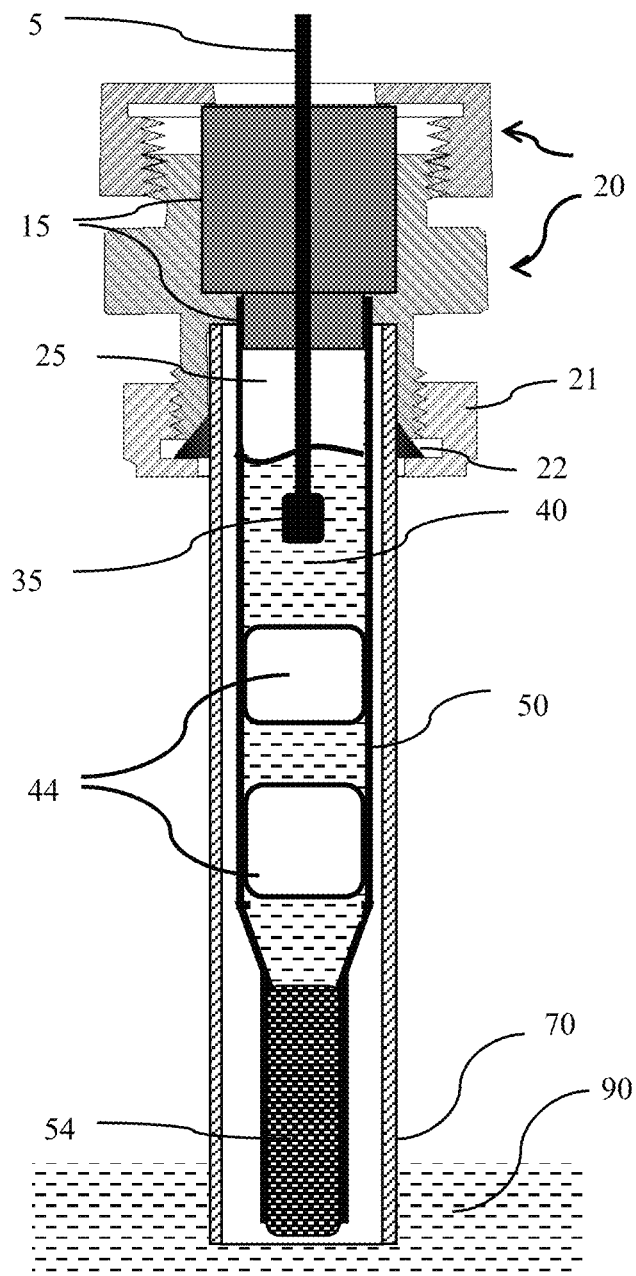
FIG. 1 illustrates the prior art of a typical tube type of high pressure reference electrode in which gas bubbles formed inside the internal electrolyte-housing tube and block the electrical continuity.

5 metal conductor connected to reference material (see 35)
6 metal conductor connected to reference material for pH electrode (see 36)
15 seals for reference electrode
16 seal for pH electrode
20 compression fitting
21 nut
22 seal for connection to a metal tubing (see 70)
25 gas space (usually air)
35 reference material (usually Ag/AgCl)
36 internal reference material for pH electrode
40 internal electrolyte for reference electrode (usually KCl solution)
41 internal electrolyte for pH electrode
44 gas bubbles formed inside internal electrolyte-housing tube
50 internal electrolyte-housing tube, usually made of heat shrink polytetrafluoroethylene (PTFE) tube
51 thin tubes or rods
54 porous liquid junction plug that allows electrical current to go through
70 tubing as electrode body that facilitates installation of electrode to a pressurized system
80 internal electrolyte-housing tube of a pH electrode
81 glass bulb of a pH electrode
90 external liquid in which the electrode is used (immersed)

DETAILED DESCRIPTIONS OF THE INVENTION

Prior Arts

FIG. 1 shows the prior art of a typical tube type of high pressure and high temperature reference electrode. The reference material (35) and the internal electrolyte (40) of the reference electrode are inside the internal electrolyte-housing tube (50). The electrical lead (5) that is connected to the reference material (35) and the internal electrolyte (40) is sealed inside the internal electrolyte-housing tube with the seals (15) by using the compression fitting (20) and the porous liquid junction plug (54). The compression fitting has a nut (21) and a metal seal (22) that are used to assemble the electrode to a metal tubing (70) that facilitates the mounting of the electrode to a high pressure system that contains the external liquid (90) in which the reference electrode is used. When the electrode is assembled, a small amount of air is usually trapped inside the internal electrolyte-housing tube at the top and forms an air space (25).

When the electrode is positioned upside down or even horizontally, the air in the air space (25) may travel to the lower section of the electrode. Because the internal electrolyte-housing tube is usually thin (<10 mm inside diameter), the air traveled to the lower section of the electrode often forms air bubbles (44) and the air bubbles (44) sometimes are trapped somewhere between the reference material (35) and the porous liquid junction plug (54) due to the surface tension. Such bubbles often cause an electrical isolation between the reference material (35) and the external liquid (90) and make the reference electrode useless.

Method to Prevent Gas Bubble Formation Inside the Internal Electrolyte-Housing Tube Oftentimes, the gas bubbles (44) as shown in FIG. 1 cannot be removed even by shaking the reference electrode. Porous materials, such as glass fiber (see S. H. Oh, C. B. Bahn, and I. S. Hwang, "Evaluation of Thermal Liquid Junction Potential of Water-Filled External Ag/AgCl Reference Electrodes," *Journal of The Electrochemical Society*, Vol. 150, page E321-E328, 2003) and zirconia sand (see A. K. Agrawal and R. W. Staele, "A Silver-Silver Chloride Reference Electrode for the High Temperature and High Pressure Electrochemistry," *Corrosion*, Vol. 33, page 418-419, 1977), were often used inside the internal electrolyte-housing tube to avoid such gas bubbles. These porous materials maintain the electrical continuity between the reference material (35) and the external liquid (90) by capillary effect that causes the liquid to be sunken into the pores of the fiber or sand.

Figure 2:
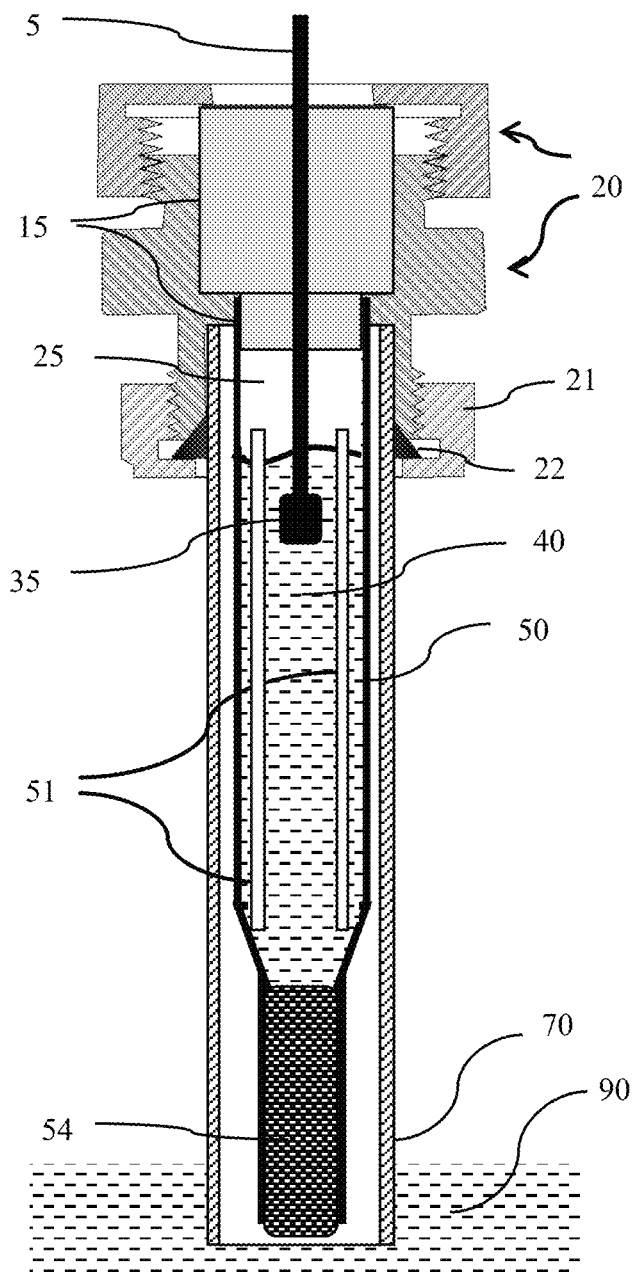
FIG. 2 illustrates a typical high pressure, high temperature reference electrode that has two thin tubes inside the internal electrolyte-housing tube to eliminate gas bubbles in the internal electrolyte.

FIG. 2 shows the new design of the reference electrode in which two pieces of thin (approximately 1 mm outside diameter) polytetrafluoroethylene (PTFE) tubing (51) was inserted inside the internal electrolyte-housing tube of a high temperature reference electrode that has a liquid junction plug (54). Unlike the glass fiber or cotton wick, the two pieces of solid tubing are not porous and they cannot be soaked by the liquid.

But the solid thin tubes break the surface tension of the air bubbles and cause the bubbles to travel to the upper location when the reference electrode is tilted or vertically placed. Thin glass rods or metal wires (stainless steel wire or silver wire) had also been tried and they were found to have similar effect of causing the bubbles to travel upward. Unlike the glass and cotton wool, which are difficult to handle (e.g., to put into a long tube) and difficult to clean, the thin PTFE tubes (or thin glass rods) are easy to use and easy to clean and provide the unanticipated benefit of maintaining the continuity between the reference material (35) and the external liquid (90).

Figure 3:
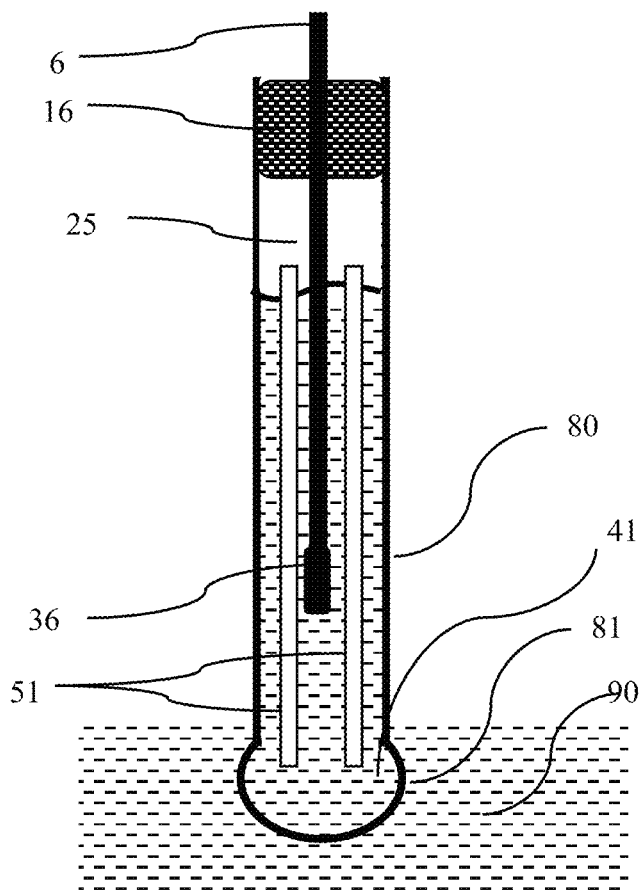
FIG. 3 illustrates a typical high pressure pH electrode that has two thin tubes inside the internal electrolyte-housing tube to eliminate gas bubbles in the internal electrolyte.

FIG. 3 shows that the two thin tubes/rods (51) were also used in a pH electrode to void the formation of gas bubbles between the reference material (36) and the glass bulb (81) of the pH electrode.

Other Embodiments

Although PTFE tubes and glass rod were used to eliminate the gas bubble formation between the reference material and the liquid junction plug inside the internal electrolyte-housing tube. It can also be any other material that is chemically, thermally, and mechanically stable at the intended use temperature. In addition, the method used to prevent the formation of the gas bubbles inside the internal electrolyte-housing tubes using thin tubes or thin rods may also be used for other systems containing a vertical or sloped liquid-filled tube.

Although the present invention has been described in detail, it should be understood that various changes, substitutions, and alterations can be made hereto, without departing from the spirit and scope of the invention as defined by the appended claims.

The invention claimed is:

1. A high pressure reference electrode comprising:
    (a) a tube for housing an internal reference electrolyte and a metal conductor connected to a reference material at the bottom of the conductor;
    (b) a liquid junction plug sealed to the bottom of the tube wherein the plug is at a substantial distance from the reference material and is in direct contact with the internal reference electrolyte and allows electrical current to go through;
    (c) seals at the top of the tube that seal the internal reference electrolyte and the reference material inside the tube and allow the metal conductor to penetrate from the upper end for electrical connection;
    (d) one or more thin and long rigid objects inside the tube wherein the one or more thin and long rigid objects extend from the reference material all the way to the liquid junction plug,
    wherein the one or more thin and long rigid objects prevent the formation of gas bubbles in the liquid section between the reference material and the liquid junction plug.

2. The high pressure reference electrode of claim 1, wherein the one or more thin and long rigid objects are made of tubing.

3. The high pressure reference electrode of claim 2, wherein the tubing is made of polytetrafluoroethylene.

4. The high pressure reference electrode of claim 1, wherein the one or more thin and long rigid objects are made of thin rod.

5. The high pressure reference electrode of claim 4, wherein the thin rod is made of ceramic material.

6. A method to avoid the formation of gas bubbles in a vertical or sloped tube containing a liquid and a gas, whereby the tube inside space is so narrow that a single gas bubble may be trapped in the narrow space and separate the liquid into two isolated sections, by inserting one or more thin and long rigid objects with a length that covers the depth of the desired bubble-free section into the tube, wherein the one or more thin and long rigid objects prevent the formation of gas bubbles that may separate the liquid into isolated sections.

7. The method of claim 6, wherein said tube is for housing the internal reference electrolyte of a pH electrode.

8. The method of claim 6, wherein the one or more thin and long rigid objects are made of thin tubing.

9. The method of claim 8, wherein the thin tubing is made of polytetrafluoroethylene.

10. The method of claim 8, wherein the thin tubing is made of metal.

11. The method of claim 8, wherein the thin tubing is made of glass.

12. The method of claim 6, wherein the one or more thin and long rigid objects are made of thin rod.

13. The method of claim 12, wherein the thin rod is made of a glass.

14. The method of claim 12, wherein the thin rod is made of a ceramic material.

15. The method of claim 12, wherein the thin rod is made of a metal.

* * * * *